United States Patent [19]

Tokish, Jr. et al.

[11] Patent Number: 5,534,005
[45] Date of Patent: Jul. 9, 1996

[54] SURGICAL MILLING SYSTEM

[75] Inventors: Leonard J. Tokish, Jr., Cordova, Tenn.; Thomas W. Fallin, Champaign, Ill.; Jeff Schryver, Cordova, Tenn.

[73] Assignee: Smith & Nephew Richards, Inc., Memphis, Tenn.

[21] Appl. No.: 318,477

[22] Filed: Oct. 5, 1994

[51] Int. Cl.⁶ .................................................. A61B 17/56
[52] U.S. Cl. ................................ 606/80; 606/79; 606/89; 606/96
[58] Field of Search ................................ 606/89, 88, 87, 606/86, 96, 80, 85, 79, 102; 623/22, 23

[56] References Cited

U.S. PATENT DOCUMENTS

| | | |
|---|---|---|
| 3,581,622 | 6/1971 | Maass . |
| 3,863,543 | 2/1975 | Böttcher et al. . |
| 3,919,919 | 11/1975 | Danesik . |
| 4,176,585 | 12/1979 | Anderson . |
| 4,197,645 | 4/1980 | Scheicher . |
| 4,279,598 | 7/1981 | Schericher . |
| 4,284,080 | 8/1981 | Rehder . |
| 4,461,082 | 7/1984 | Nissman . |
| 4,466,429 | 8/1984 | Loscher et al. . |
| 4,777,942 | 10/1988 | Frey et al. . |
| 4,790,852 | 12/1988 | Noiles ........................................ 623/18 |
| 5,047,033 | 9/1991 | Fallin ........................................ 606/87 |
| 5,129,907 | 7/1992 | Heldreth et al. ........................... 606/80 |
| 5,190,547 | 3/1993 | Barber, Jr. et al. ........................ 606/79 |
| 5,250,050 | 10/1993 | Poggie et al. .............................. 606/79 |
| 5,387,218 | 2/1995 | Meswania .................................. 606/80 |
| 5,403,320 | 4/1995 | Luman et al. ............................. 606/89 |

FOREIGN PATENT DOCUMENTS

| | | |
|---|---|---|
| 2255996 | 7/1975 | France . |
| 2329454 | 5/1977 | France . |
| 2848602 | 6/1980 | Germany . |
| 3538654 | 4/1987 | Germany .................................. 606/96 |
| 1394799 | 5/1975 | United Kingdom . |
| 1482848 | 8/1977 | United Kingdom . |

*Primary Examiner*—Guy Tucker
*Attorney, Agent, or Firm*—Pravel, Hewitt, Kimball & Krieger

[57] ABSTRACT

An in-situ surgical orthopedic milling apparatus includes an instrument frame having upper and lower end portions. A plurality of templates are provided, each forming a respective virtual pattern. A cutting device supported upon the frame cuts bone tissue (e.g., within the intramedullary canal of a patient's bone), by tracking the virtual patterns. A system of vertically stacked templates can be placed in position with respect to the instrument frame to define an operative position. The templates provide a wall portion that constrains movement of the cutting tool beyond a desired surgical cutting area defining an "actual pattern". In this first embodiment, the templates are in the form of stacked templates, each template having its own pattern.

12 Claims, 9 Drawing Sheets

SURGICAL MILLING SYSTEM

BACKGROUND OF THE INVENTION

1. Field of the Invention

The present invention relates to surgical orthopedic instrumentation and more particularly relates to an improved method and apparatus for milling a patient's bone tissue with instrumentation that can ream a patient's intramedullary canal in-situ during orthopedic surgery. A pattern constrains movement of a cutting tool, or a tracing stylus rigidly affixed to the cutting tool. Inadvertent travel of the cutting tool beyond the cutting field is prevented by the pattern.

2. General Background

There are existing milling devices used to prepare the femur prior to surgical implantation of a hip prosthesis. Attempts have been made in the past to automate the milling process. One such robotic product from Integrated Surgical Systems, Inc. is a product known by the trademark as "Robodoc".

Some patents have been issued which relate generally to milling instrumentation that includes a guiding system.

The Sulzer U.S. Pat. No. 4,777,942 discloses a surgical instrument for inner femur cutting. The '942 patent discloses a milling cutter on a spindle, joined to a gauge, with the spindle ending in a shoe. The apparatus of the '942 patent provides a curved instrument for cutting a curved contour inside the cavity of the femur.

U.S. Pat. No. 4,284,080 discloses a ball and socket insertion for hip joint prosthesis using curved cutters of a milling tool to shape the convex surface of the femur.

U.S. Pat. Nos. 4,197,645 and 4,279,598 issued to H. Scheicher each disclose a bone cavity milling head which has two cutters on offset axes driven at the same time.

U.S. Pat. No. 4,466,429 discloses a bone recess forming instrument which incorporates a machine driven tool having two rasp halves shaped to suit the recess.

French patent 223972 issued to Ceraver discloses an artificial hip joint fitting apparatus that includes a drilling jig in a round cutter head for a retaining boss socket.

The Kuhlmann British patent GB1394799 discloses a milling machine controlled by a pantograph. Kuhlmann also received a patent for a pattern controlled milling machine with a pantograph and line scanner, U.S. Pat. No. 3,581,622.

British patent GB1482848 discloses a templet control mechanism for a shoe upper milling machine. The mechanism is constructed to simplify set-up and operation. A vertical stack of different templates is provided to be contacted by one or more moving styli. The tool involved traces the templet outline on a shoe upper.

French patent 7533306 has been assigned to A. Lora that allows accurate and rapid tracing of ellipses of all sizes. It has slides in guides at right angles to each other.

R. Lopez was assigned patent FR2255996 on a machine for reproducing models through the use of a motor driven slide system for tracing a finger-controlling tool.

A German patent, DE2,848,602 was issued to Karl Harlan for a copying pantograph for milling small work pieces. It can be operated with a hand held power drill mounted in a U-shaped bracket.

U.S. Pat. No. 4,176,585 discloses a universal pantograph pattern with a number of interconnected arms, and a cutting tool for milling circular and eccentric shapes, angles, and lines.

U.S. Pat. No. 3,919,919 discloses a three dimensional cutting machine with pantograph control.

U.S. Pat. No. 3,863,543 discloses a pattern transmitting device for three dimensional working. The apparatus includes a drawing reader which follows the outline of a drawing controlling the pantograph and tracer.

U.S. Pat. No. 4,461,082 discloses a pantograph mechanism for an engraving machine. The machine is pivoted to slide about a vertical axis, with the tool holder prevented from pivoting.

U.S. Pat. No. 4,790,852 includes a description of canal preparation which are essentially a match to the shape of a modular sleeve.

Two recently issued patents that relate to bone milling include U.S. Pat. No. 5,047,033 issued to Fallin and assigned to the assignee of this application. The other recently issued patent relating to milling is U.S. Pat. No. 5,190,547 issued to Barber, Jr. et al. entitled "Replicator For Resecting Bone to Match a Pattern". The '547 patent relates to a device for resecting a bone utilizing a pattern to control the cutting tip for the resection. The device has a frame with a pattern holder and a bone holder. A tool holder mounts to the frame by means of a four bar linkage assembly. The tool holder has a cutting tool and a probe mounted to it. The four bar linkage allows two dimensional movement of the tool holder, but constrains the tool holder to always be in parallel with a line extending through the pattern holder and bone holder.

SUMMARY OF THE PRESENT INVENTION

The present invention provides a surgical orthopedic milling apparatus and method. The apparatus includes an instrument frame having upper and lower end portions.

In one embodiment, a system of vertically stacked templates provides an in-line segmental system which provides one or a plurality of templates that are moved into the operative area one at a time. Each segment or template provides a different preselected pattern. The vertically stacked template system allows segments that are not being used to be removed from the operative area adjacent the instrument frame. A cutting device is supported upon a stabilizing device that is supported upon the template and/or frame for cutting bone tissue within the intramedullary canal of a patient's bone. An indexing system affixes a selected template to the instrument frame at a selected elevational position to define an operative position. A vertical stabilizer/coupling tool supports a cutting instrument such as a reamer for tracking a pattern.

A plurality of templates provide a corresponding plurality of respective virtual patterns.

A cutting device supported upon the frame provides for cutting bone tissue within the intramedullary canal of a patient's bone. An indexing system affixes a selected template to the instrument frame at a selected elevational position to define an operative position.

Another embodiment of the present invention provides a pantographic monolithic system. The apparatus includes a pattern in the form of a monolithic structure defining a constraint to the tracing stylus affixed to the cutting instrument, thereby preventing inadvertent movement of the cutting instrument beyond the desired cutting area.

A third embodiment of the present invention provides a dual pattern monolithic system. The apparatus includes two identical patterns in the form of monolithic structures defining a constraint for each of two tracing styli affixed to a single cutting instrument, thereby preventing inadvertent movement of the cutting instrument beyond a desired cutting area defined by the two patterns.

With the vertically stacked template, pantographic monolithic, and dual pattern monolithic systems, cutting is constrained within a pattern (or patterns) to prevent inadvertent movement of the cutting tool (reamer or mill) beyond the desired area to be cut, as defining a cutting path to be cut within the patient's femur for example.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

FIGS. 1–11 illustrate generally the preferred embodiment of the apparatus of the present invention designated generally by the numeral 10.

In-line segmental mill apparatus 10 includes an alignment frame 15 that can be affixed to the proximal 12 end portion of a patient's femur 11. The patient's femur 11 has a central longitudinally extending intramedullary canal 13 that is to be cut, following an actual pattern. The actual pattern to be cut traces the outer configuration of a femoral implant that is to be surgically placed. The patient's femur 11 provides an outer surface 14, a medial portion 16 and proximal end 12.

Alignment frame 15 includes a cylindrical pin 17 that anchors alignment frame 15 to the patient's femur 11, occupying a surgically formed opening 41.

Cylindrical pin 17 can be attached integrally to column 18. Column 18 has an upper end 20 and a lower end 19. The outer surface 21 of column 18 is preferably generally cylindrically shaped.

Vertical web member 22 extends laterally from column 18 as shown in FIGS. 1–5. Web 22 has an upper end 23 and a lower end 24. A plurality of shoulders 25–40 are in web 22, and each defines a place for registration of one of a plurality of templates (such as templates 42, 47, 61) thereto. Each of a plurality of templates (such as 42, 47, 61) attaches to a different one of the plurality of shoulders 25–40. Thus, for each of the shoulders 25–40, there is a corresponding template such as template 42, 47, 61 and each template of a different size and shape.

In the embodiment shown, there are sixteen (16) shoulders 25–40. Similarly, there would be sixteen (16) templates, each sized and shaped respectively to register upon a particular one of the shoulders 25–40.

Each template 42 (see FIG. 6) is comprised of a horizontal flange portion or rail 43 having an upper surface 43a and lower surface 43b. Rail 43 supports hollow bushing 44 which extends above and below flange 43. The bushing 44 has a vertical, open ended bore 51 and a vertical slot 65 that communicates with slot 46 of template 42. When a particular template (e.g. template 42) is placed upon column 18 and web 22, bushing 44 surrounds and is laterally supported upon column 18. Column 18 occupies opening 51. Webb 22 occupies vertical slot 65 and horizontal slot 46. Template 42 rests upon a shoulder such as 40.

Template 42 includes an opening in the form of pattern 45. The pattern 45 is formed of a desirable size and shape and is tracked by a cutting instrument such as reamer 52 during use. Other templates include other patterns of selected size and shape (e.g. patterns 50, 64 in FIGS. 7 and 8).

Template 42 also includes a rectangular slot 46. Each of the rectangular slots 46 of a particular template is of a different size. The slots 46 are progressively longer corresponding with shoulder 25 and ending with shoulder 40, so that the shortest rectangular slot 51 registers the first template upon the highest shoulder 25. The slots 46 are sized and shaped to register additional templates in sequence upon the different shoulders 25–40. In this fashion, a corresponding template having a rectangular slot (such as slot 46) is sized and shaped differently to fit each of the shoulders 25–40 respectively.

Figure 6:
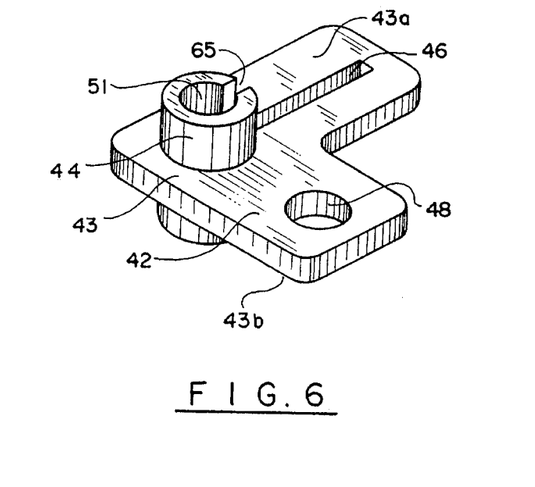
FIG. 6 is a fragmentary perspective view of a template portion of the preferred embodiment of the apparatus of the present invention.
Figure 7:
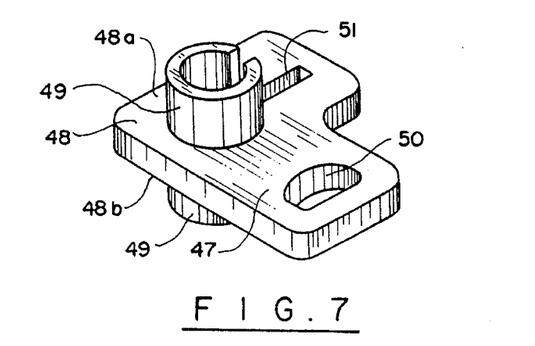
FIG. 7 is a fragmentary perspective view of another template portion of the preferred embodiment of the apparatus of the present invention.
Figure 8:
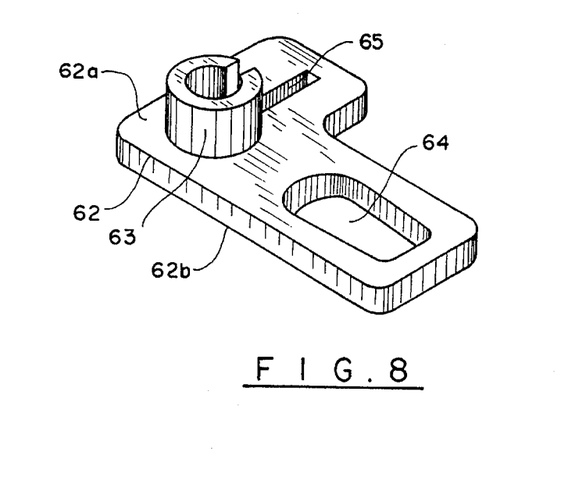
FIG. 8 is a fragmentary perspective view of yet another template portion of the preferred embodiment of the apparatus of the present invention.
Figure 9:
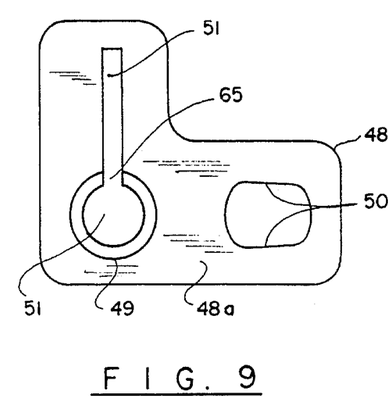
FIG. 9 is a top fragmentary view of the preferred embodiment of the apparatus of the present invention illustrating a template portion thereof.
Figure 10:
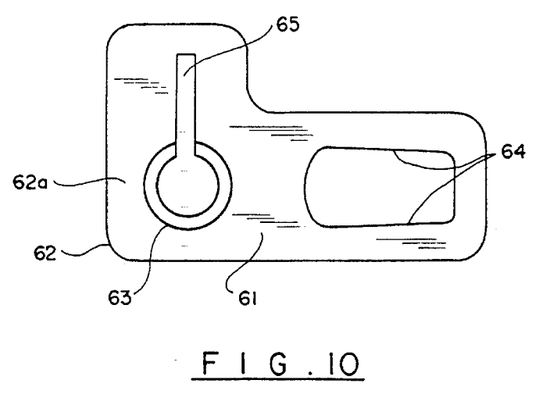
FIG. 10 is a top fragmentary view of the preferred embodiment of the apparatus of the present invention illustrating a template portion thereof.
Figures 11A, 11B, 11C, 11D:
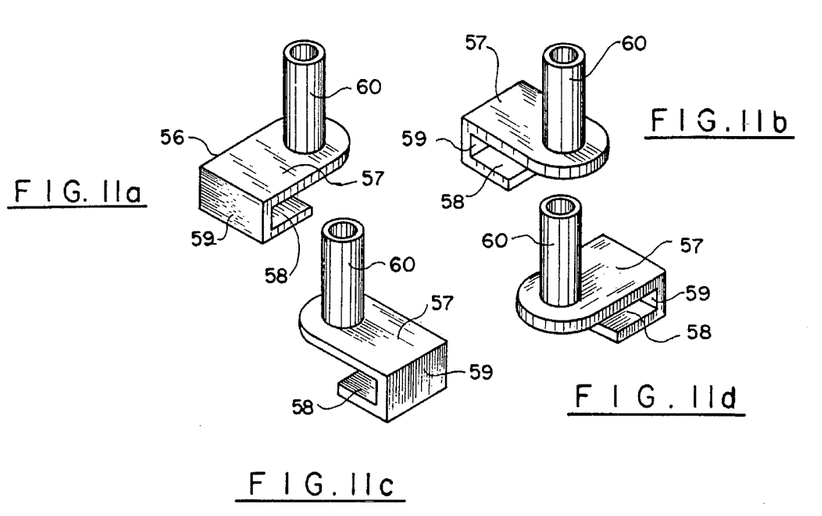
FIGS. 11A–11D are perspective views of the template system vertical stabilizer/coupling tool for the vertically stacked portion of the preferred embodiment of the apparatus of the present invention.

The smallest template has been indicated with the number 42 (FIG. 6). The largest template has been indicated by the number 61 (FIG. 8). The template 42 rests upon the lowest shoulder 40 while the template 47 rests upon the highest shoulder 25. The template 47 provides a flange or rail 48, upper and lower surfaces 48a, 48b respectively, and cylindrically shaped bushing 49. Template 47 provides a pattern 50 that is of a particular selected size and shape. The template 47 provides rectangular slot 51 that is sized and shaped to fit web 22 and shoulder 25.

Figure 1:
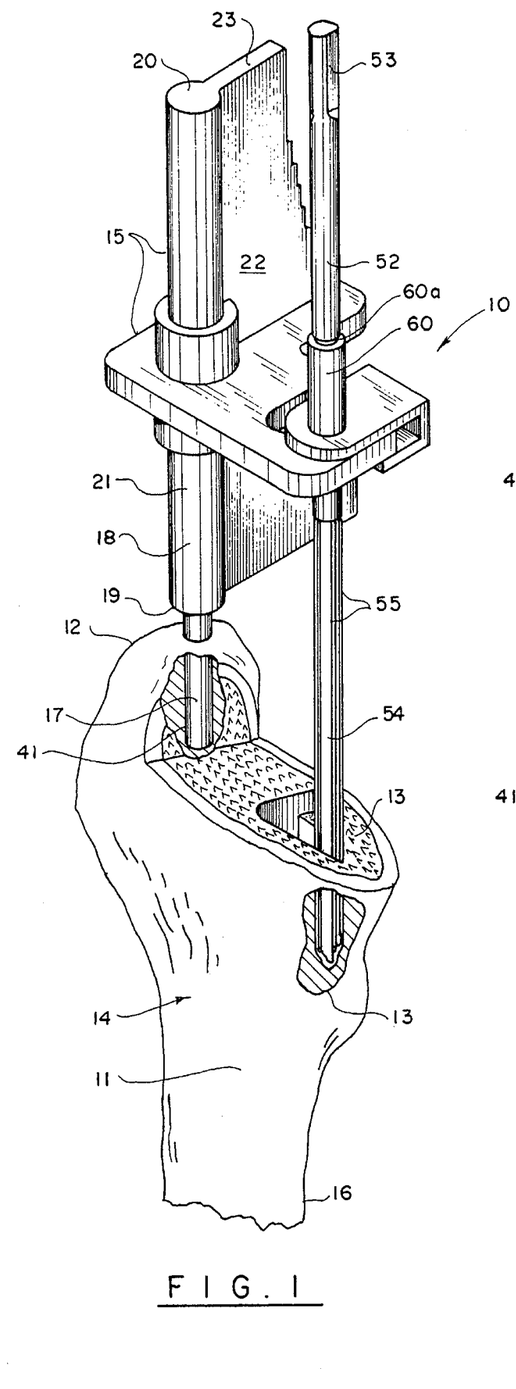
FIG. 1 is a perspective view of the preferred embodiment of the apparatus of the present invention.
Figure 2:
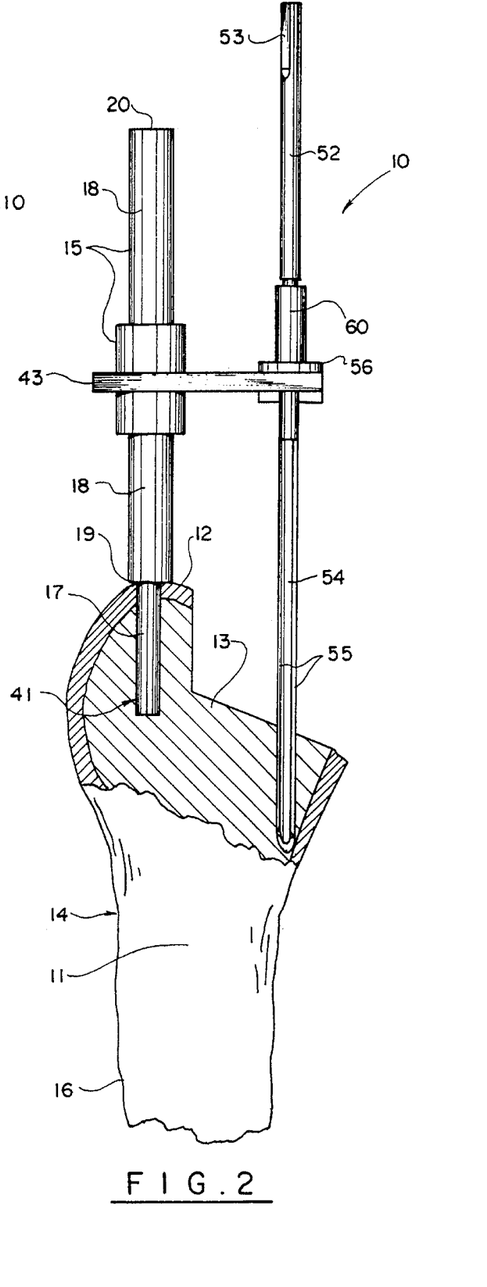
FIG. 2 is a sectional anterior view of the preferred embodiment of the apparatus of the present invention.
Figure 3:
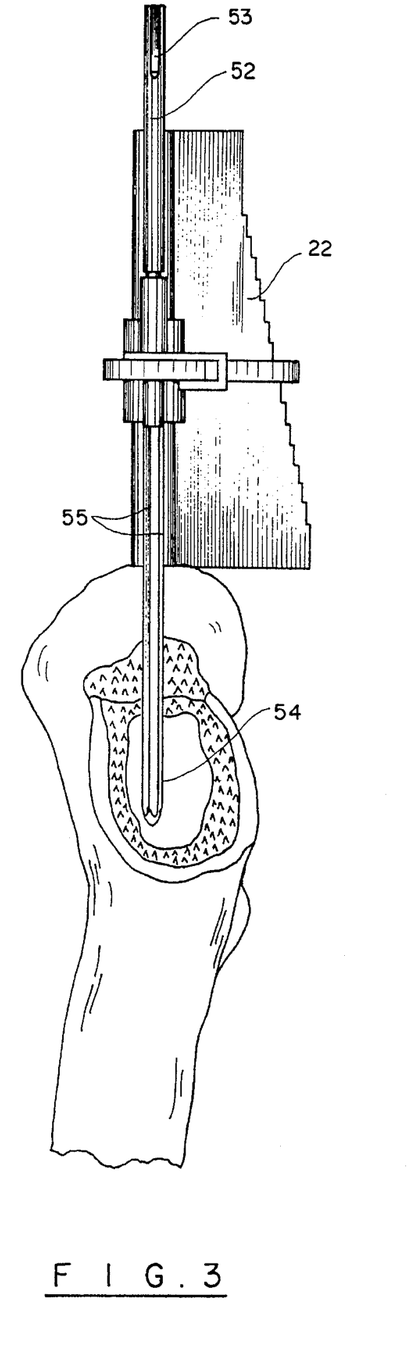
FIG. 3 is a medial view of the preferred embodiment of the apparatus of the present invention shown in use during surgical cutting of a patient's intramedullary canal.
Figure 4:
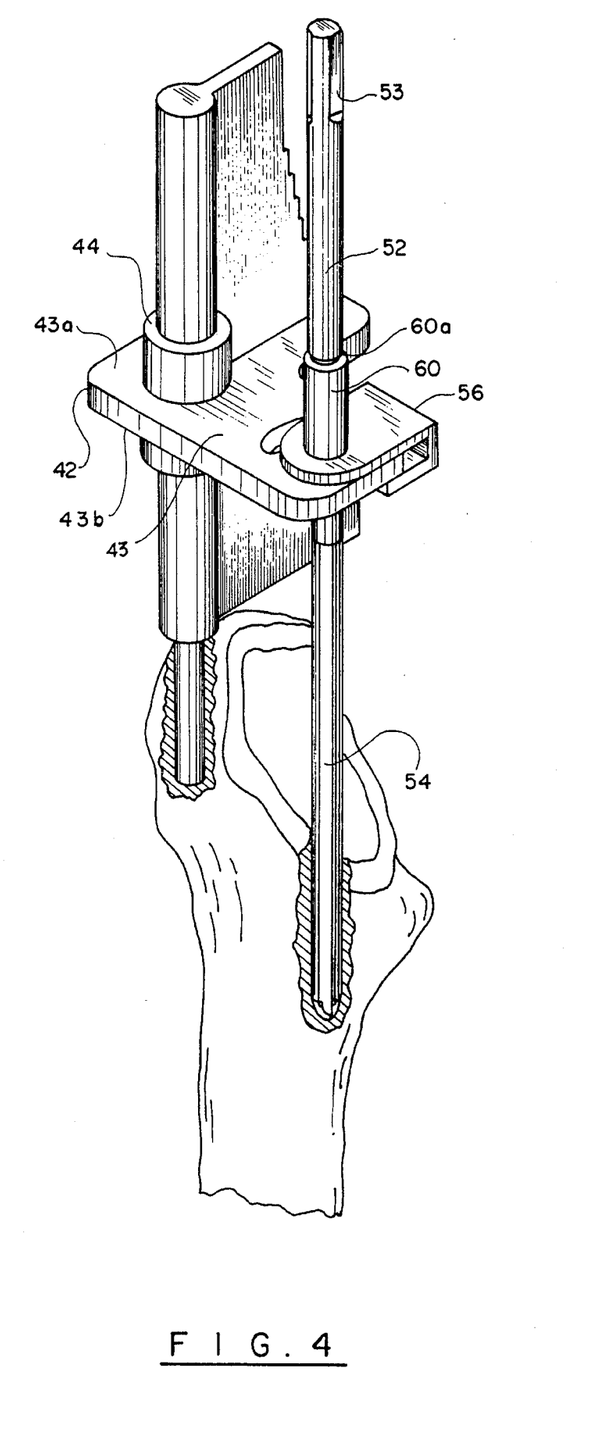
FIG. 4 is a perspective view of the preferred embodiment of the apparatus of the present invention.
Figure 5:
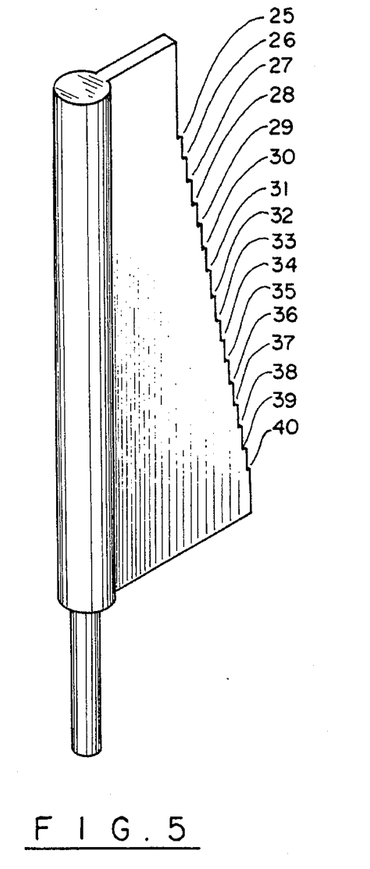
FIG. 5 is a partial perspective view of the preferred embodiment of the apparatus of the present invention illustrating the alignment frame portion thereof.

In FIGS. 2–4, reamer 52 is shown in operative position after frame 15 has been anchored at pin 17 to the proximal end 12 of femur 11. Reamer 52 provides a plurality of tool flats 53 at the upper end portion thereof. Reamer 52 provides a cutting end portion 54 at its lower end portion that includes a plurality of cutting elements 55.

Vertical stabilizer 56 supports reamer 52 and includes upper plate 57, lower plate 58, and vertical plate 59. Stabilizer 56 also includes cylindrically shaped hollow bushing 60 that provides an internal bore 60a with an internal diameter closely conforming to the external surface of reamer 52, supporting reamer 52 but allowing rotation of reamer 52. The reamer 52 can rotate with respect to bushing 49 and vertical stabilizer 56 during the cutting operation. Vertical movement is constrained, however, by the template and stabilizer. The reamer 52 can have a larger diameter above and/or below the bushing so that it is constrained vertically.

In FIG. 8, template 61 includes flange 62, upper and lower surfaces 62a, 62b, bushing 63 and rectangular slot 65. Template 61 provides a larger pattern 64 to illustrate a larger and different shape than those of templates 42 and 47 shown in FIGS. 6 and 7. Thus, by stacking a plurality of templates (including templates 42, 47, 61 and others as desired) in a desired sequence and at selected positions upon alignment frame 15, a surgeon can define a three dimensional virtual pattern to be tracked in sequence by the reamer 52.

The elevational position of each of the templates (such as 42, 47, 61) is controlled by the shoulders 25–40 of the alignment frame 15. In this fashion, a particular actual pattern can be formed in the patient's intramedullary canal 13 using a plurality of segments provided by the plurality of templates as aforedescribed. This allows custom shaping of an actual pattern in a patient's femur to accept a particular prosthesis that has been selected by the surgeon for a particular patient.

FIGS. 12–15 illustrate a second embodiment of the apparatus of the present invention designated generally by the numeral 66. Pantographic milling apparatus 66 includes an alignment frame 67 that is supported upon a patient's femur 11 using base 68. Base 68 includes a pair of arms 69, 70 that can be placed opposite each other and about femur 11, for gripping the exterior surface 14 of the patient's femur 11. Base 68 can be attached to femur 11 using bone pins inserted through openings in base 68 and into the femur 11.

Alignment frame 67 includes column 71 having an upper end portion 72 and a lower end portion 73. Opening 74 in clamp 68 allows attachment of column 71 thereto. The lower end 73 of column 71 fits tightly into opening 74 upon assembly (using a threaded connection for example).

Pattern body 75 is affixed to column 71 and supported by column 71 during use. Pattern body 75 provides a bore 76 that defines a virtual pattern for stylus 81 as will be described more fully hereinafter. Pattern body 75 includes a continuous wall 77 that surrounds bore 76, thus defining the virtual pattern that is to be tracked by the stylus 81 during bone cutting operations.

Column 71 assembles to pattern body 75 at cylindrically shaped vertical channel 78. The channel 78 can simply conform to the outer surface of the column 71. Body 75 can be affixed rigidly to column 71 by welding, set screws, a temporary locking mechanism, or the like. Pattern body 75 includes an upper surface 79 and a lower surface 80. The channel 78 extends through the pattern body 75 between the upper surface 79 and the lower surface 80.

Figure 13:
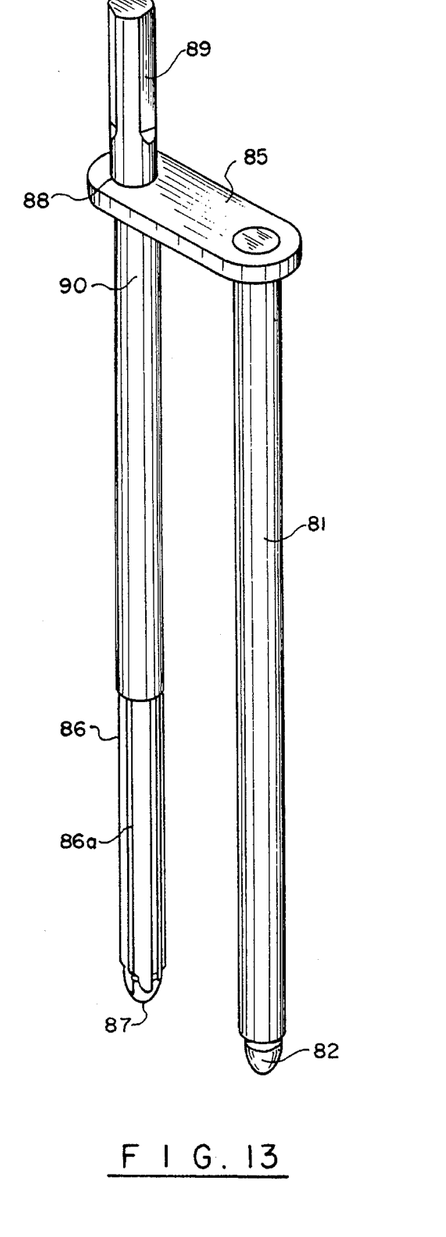
FIG. 13 is a partial perspective view of the second embodiment of the apparatus of the present invention illustrating the rigidly fixed tracing stylus and cutting instrument.
Figure 14:
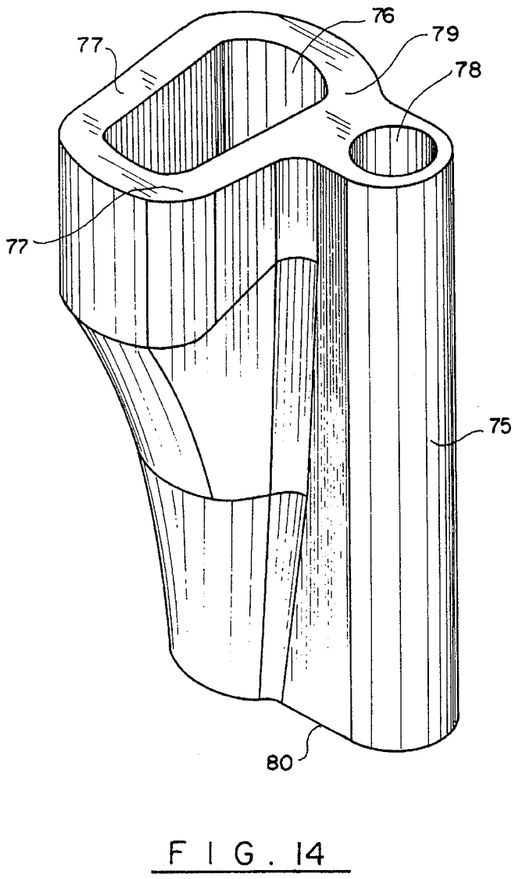
FIG. 14 is a partial perspective view of the second embodiment of the present invention illustrating the cutting guide portion thereof.

In FIG. 13, stylus 81 is maintained in generally parallel relationship with a cutting tool 86, (e.g. a reamer). Stylus 81 includes a lower end portion 82 that tracks the virtual pattern of bore 76. Upper end portion 83 of stylus 81 attaches at opening 84 to upper stabilizer/coupling tool 85.

Reamer 86 includes a lower end 87 having cutting portions thereon and an upper end 90 that attaches to upper stabilizer/coupling tool 85 at opening 88. The upper end portion 90 of reamer 86 can provide a plurality of tool flats 89 for attaching a motor drive thereto.

Figure 12:
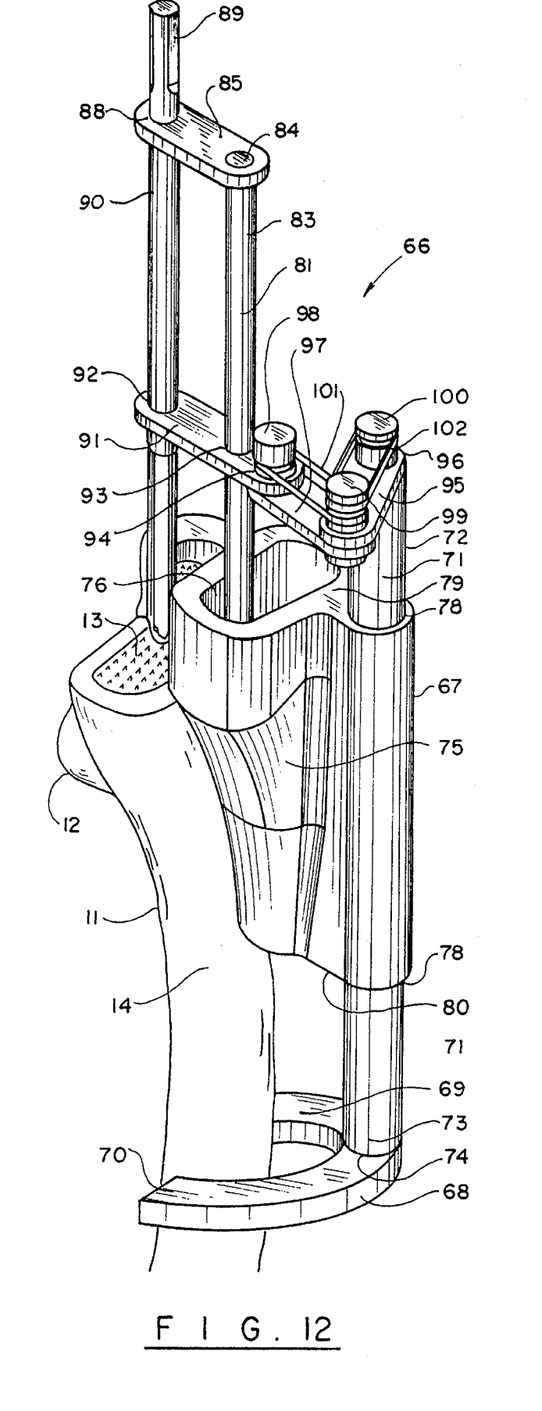
FIG. 12 is a perspective view of a second embodiment of the apparatus of the present invention.
Figure 15:
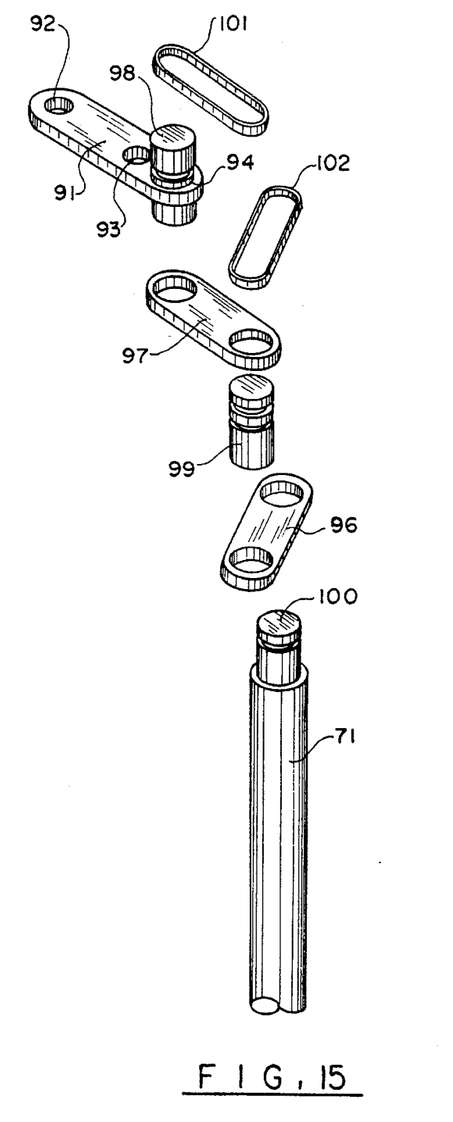
FIG. 15 is a partial perspective exploded view of the second embodiment of the apparatus of the present invention.

In FIGS. 12 and 15, lower stabilizer/coupling tool 91 forms a connection between stylus 81 and reamer 86. The lower stabilizer/coupling tool 91 forms a connection at opening 92 with cutting tool/reamer 86. Lower stabilizer/coupling tool 91 forms a connection at opening 93 with stylus 81.

In another embodiment of the reamer 86, the cutting portion 86a may be the only portion of the reamer 86 that actually rotates. This can be illustrated by reamer 86 being rigidly affixed to coupling tool 85. Flats 89 may be eliminated from the concept. Cutting portion 86a may be attached to reamer 86 in such a way that the cutting portion 86a could be attached to a motor, allowing it to freely rotate with respect to upper end 90.

Lower stabilizer/coupling tool 91 provides opening 94 for attaching tracing apparatus 95 thereto. Tracing apparatus 95 comprises a pair of link members 96, 97 and a plurality of pivots 98–100. A pivotal connection is formed between lower stabilizer/coupling tool 91 and link member 97. A pivotal connection is formed between the link member 96 and link member 97. Pivots 98–99 are engaged by endless cables 101. The pivots 99–100 are connected with cable 102. Pivot 98 may be rigidly attached to coupler 91, pivot 99 to arm 97, and pivot 100 to link 96. This allows the pivots to rotate with the bodies to which they are attached. As a pivot/body rotates, the belts attached will rotate the other pivots/bodies.

During use, the user simply tracks the virtual pattern defined by bore 76 with stylus 81. Because the virtual pattern is in the form of a hollow bore 76 surrounded by wall 77, the surgeon's field of cut is constrained by the wall 77. This constraint prevents an inadvertent movement of the cutting tool or reamer 86 beyond the desired actual pattern area. There is no danger that the surgeon will cut too much bone tissue using the apparatus of the present invention. Stylus 81 is always constrained by the wall 77 and the spacial configuration of the bore 76.

The upper and lower stabilizers 85, 91 insure that the stylus 81 and cutting tool 86 will always be maintained in fixed, desired positions with respect to each other. The same constraint is afforded with the embodiment of FIGS. 1–11. The pattern 45 is surrounded by the horizontal flange or rail 43 to prevent inadvertent movement of the cutting instrument beyond the desired actual pattern area.

Figure 16:
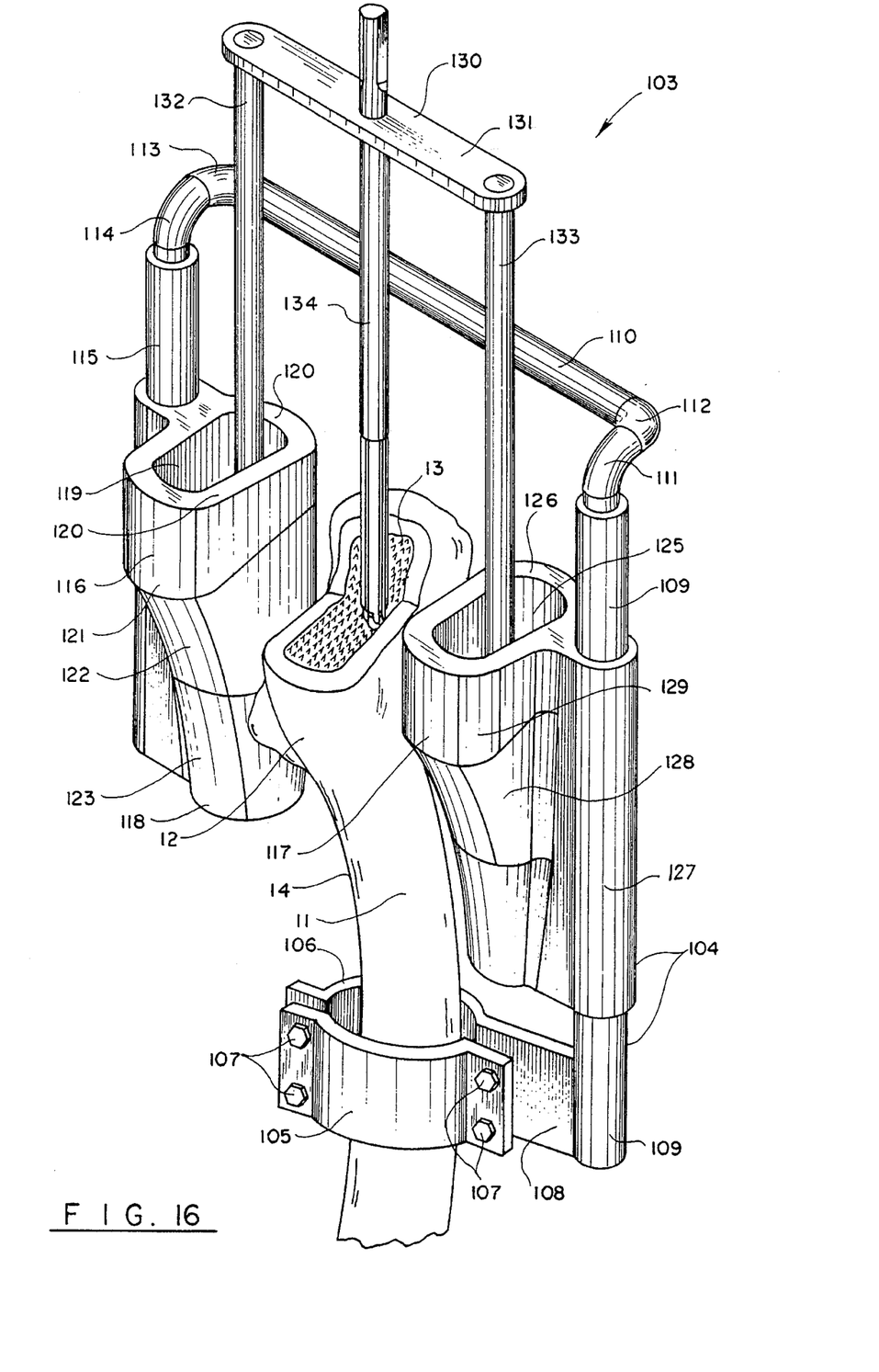
FIG. 16 is a perspective view of a third embodiment of the apparatus of the present invention.
Figure 17:
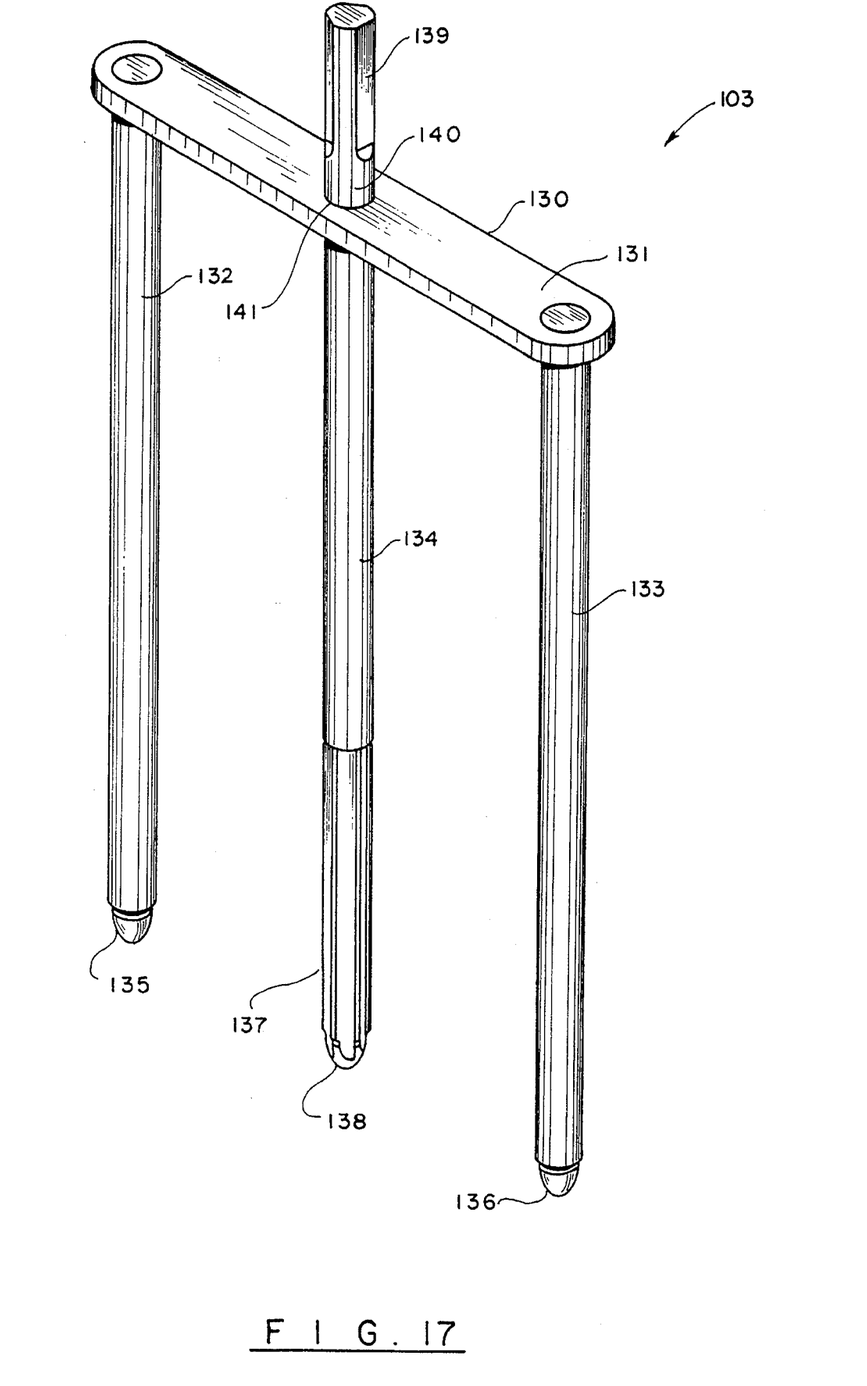
FIG. 17 is a partial perspective view of the third embodiment of the apparatus of the present invention.
Figure 18:
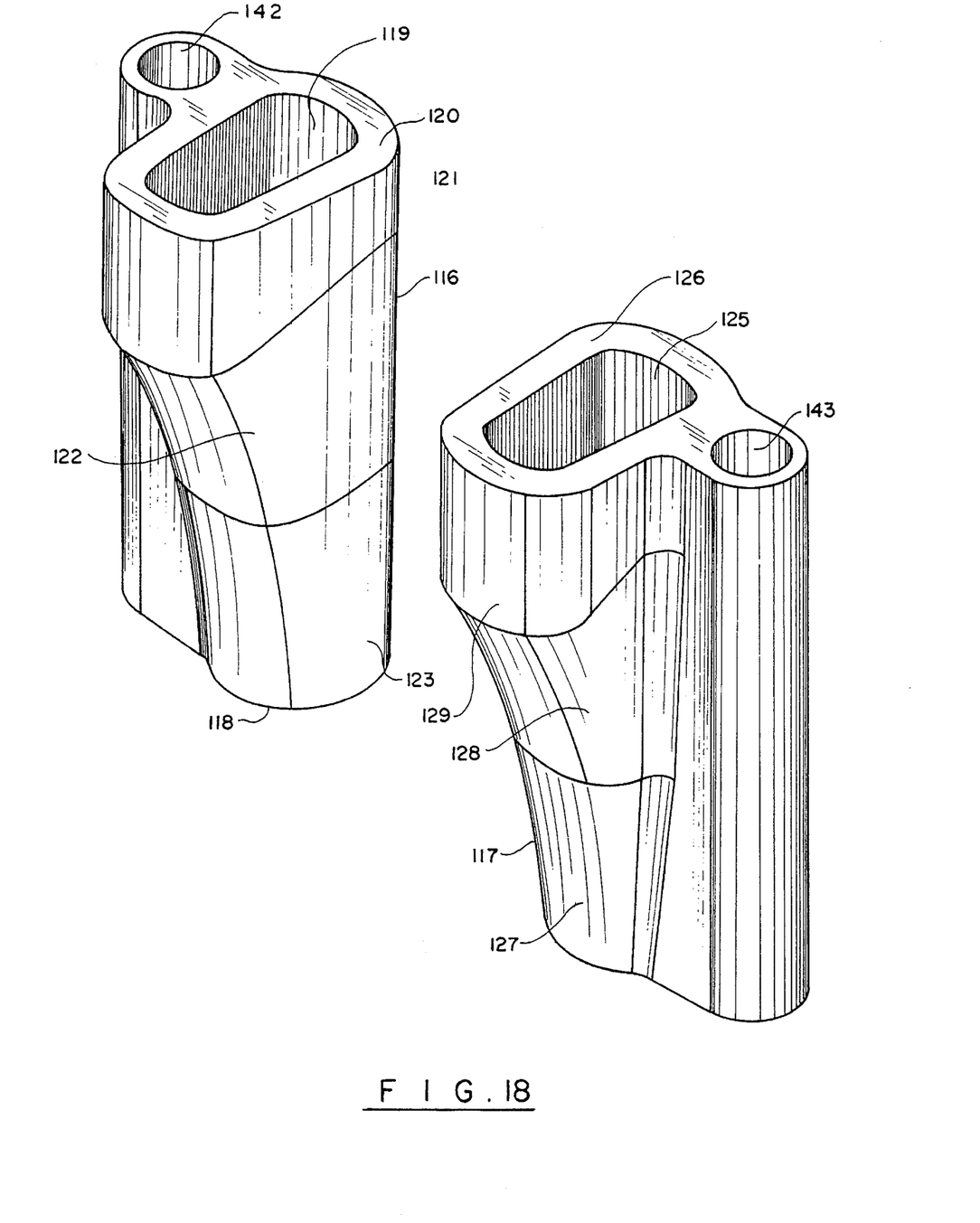
FIG. 18 is another partial perspective view of the third embodiment of the apparatus of the present invention.

FIGS. 16–18 show a third embodiment of the apparatus of the present invention designated generally by the numeral 103.

Mill apparatus 103 includes a frame 104 that can be supported upon the patient's femur 11 by clamping to the outside surface 14 thereof as shown in FIG. 16. The frame 104 has at its lower end portion a pair of U-shaped clamp members 105, 106 that can be connected together using a plurality of bolts 107 for example. The clamp member 106 has an extension 108 that connects to the lower end of post 109. Post 109 extends upwardly, generally parallel to the patient's femur as shown in FIG. 16. The post 109 is joined to another post 115 with cross bar 110 and a plurality of elbow joints 111–114 as shown in FIG. 16.

Each post 109, 115 respectively supports a pattern body 116, 117. The pattern body 116 has a lower end portion 118 that is closed, defining a bottom of pattern body 116. In FIG. 16, the pattern body 116 has a larger upper end 121, a transitional mid section 122 and a lower end portion 123 that connects to the mid section 122. Each of these body sections 121–123 is hollowed, providing an opening 119 of desired size and shape. The opening 119 is tracked by a stylus 132 during use. Outer wall 120 of pattern body 116 surrounds the central hollowed opening 119 as shown.

A second pattern body 117 is shown in FIG. 16, generally opposite the pattern body 116 with femur 11 therebetween. The pattern body 117 has a closed lower end 124 that is a closed bottom portion of the pattern body 117. As with the pattern body 116, an outer wall 126 defines a central hollowed opening 125 that defines an area to be tracked by a stylus 133. In the embodiment of FIG. 16, the pattern body 117 has a larger upper end 129, a mid section 128 and a lower section 127. Each of the openings 119, 125 respectively accommodates a stylus 132, 133. Each stylus 132, 133 is attached at its upper end to support bar 131 of an overall cutting assembly 130 that includes the stylus 132, the stylus 133, and a rotary reamer 134 positioned therebetween. The rotary reamer is rotatably mounted to cross bar 131 at rotary joint 141. Each stylus 132, 133 has a respective lower end 135, 136. Each stylus 132,133 and its lower end 135, 136 is generally smooth, for tracking the walls 120, 126 during use. Thus, the reamer 134 forms an opening in the intramedullary canal 13 of the patient's femur 11 that is sized and shaped to the corresponding openings 119,125 of the pattern bodies 116, 117. The rotary reamer 134 has a smooth, hemispherically shaped lower end 138 and a plurality of circumferentially spaced, longitudinally extending cutter blades 137. At its upper end 140, the rotary reamer provides a plurality of circumferentially spaced, longitudinally extending flats 139 that aid in attaching the reamer 134 to a power drill unit.

Each embodiment of the present invention can be manufactured of any suitable structurally sound surgical instrument material such as stainless steel or the like.

The following table lists the part numbers and part descriptions as used herein and in the drawings attached hereto.

| PARTS LIST | |
|---|---|
| Part Number | Description |
| 10 | in line segmental mill |
| 11 | femur |
| 12 | proximal end |
| 13 | intramedullary canal |
| 14 | outer surface |
| 15 | alignment frame |
| 16 | medial portion |
| 17 | cylindrical pin |
| 18 | column |
| 19 | lower end |

| PARTS LIST | |
|---|---|
| Part Number | Description |
| 20 | upper end |
| 21 | outer surface |
| 22 | vertical web |
| 23 | upper end |
| 24 | lower end |
| 25–40 | shoulder |
| 41 | surgically formed opening |
| 42 | template |
| 43 | horizontal flange or rail |
| 43a | upper surface |
| 43b | lower surface |
| 44 | cylindrical bushing |
| 45 | pattern |
| 46 | rectangular slot |
| 47 | template |
| 48 | flange or rail |
| 48a | upper surface |
| 48b | lower surface |
| 49 | bushing |
| 50 | pattern |
| 51 | rectangular slot |
| 52 | reamer |
| 53 | tool flats |
| 54 | cutting end portion |
| 55 | cutting elements |
| 56 | vertical stabilizer |
| 57 | upper plate |
| 58 | lower plate |
| 59 | vertical plate |
| 60 | bushing |
| 60a | bore |
| 61 | template |
| 62 | flange |
| 62a | upper surface |
| 62b | lower surface |
| 63 | bushing |
| 64 | pattern |
| 65 | rectangular slot |
| 66 | pantographic milling apparatus |
| 67 | alignment frame |
| 68 | base |
| 69 | arm |
| 70 | arm |
| 71 | column |
| 72 | upper end |
| 73 | lower end |
| 74 | opening |
| 75 | pattern body |
| 76 | bore |
| 77 | wall |
| 78 | vertical channel |
| 79 | upper surface |
| 80 | lower surface |
| 81 | stylus |
| 82 | lower end |
| 83 | upper end |
| 84 | opening |
| 85 | upper stabilizer/coupling body |
| 86 | reamer |
| 86a | cutting portion |
| 87 | lower end |
| 88 | opening |
| 89 | tool flats |
| 90 | upper end |
| 91 | lower stabilizer/coupling tool |
| 92 | opening |
| 93 | opening |
| 94 | opening |
| 95 | tracing apparatus |
| 96 | link |
| 97 | link |
| 98 | pivot |
| 99 | pivot |
| 100 | Pivot |

-continued

PARTS LIST

| Part Number | Description |
| --- | --- |
| 101 | cable |
| 102 | cable |
| 103 | mill apparatus |
| 104 | frame |
| 105 | clamp |
| 106 | clamp |
| 107 | bolt |
| 108 | extension |
| 109 | post |
| 110 | cross bar |
| 111 | elbow |
| 112 | elbow |
| 113 | elbow |
| 114 | elbow |
| 115 | post |
| 116 | pattern body |
| 117 | pattern body |
| 118 | lower end |
| 119 | opening |
| 120 | side wall |
| 121 | larger end |
| 122 | mid section |
| 123 | smaller end |
| 124 | lower end |
| 125 | opening |
| 126 | side wall |
| 127 | smaller end |
| 128 | mid-section |
| 129 | larger end |
| 130 | cutting assembly |
| 131 | support bar |
| 132 | stylus |
| 133 | stylus |
| 134 | rotary reamer |
| 135 | lower end |
| 136 | lower end |
| 137 | cutting blade |
| 138 | lower end |
| 139 | flat surface |
| 140 | upper end |
| 141 | rotary connection |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An in-situ surgical orthopedic milling apparatus comprising:
   a) an instrument frame having upper and lower end portions;
   b) a movable cutting instrument for cutting a patient's bone tissue;
   c) a plurality of template means having a corresponding plurality of respective patterns which constrain the cutting instrument movements, each template means defining a plane and including a top portion, a bottom portion and a peripheral portion;
   d) the cutting instrument including means for cutting bone tissue within the intramedullary canal of a patient's bone;
   e) a stabilizing means for selectively maintaining an orthogonal relationship between the cutting instrument and the plane of the template;
   f) indexing means for affixing a selected template means to the instrument frame at a selected elevational position to define an operative position;
   g) at least some of template means being removable from an operative position upon the frame when another template means is in the operative position; and
   h) means for supporting the instrument frame in-situ in a position adjacent to a patient's bone to be milled.

2. The surgical orthopedic milling apparatus of claim 1 wherein the instrument frame includes a vertically extending member having a plurality of shoulders thereon.

3. The apparatus of claim 1 wherein the instrument frame comprises a column member and a flange member extending along the side of the column member, the flange member providing a plurality of shoulders, each shoulder being at a different elevation, and each shoulder being spaced by a different dimension from the longitudinal central axis of the column.

4. The apparatus of claim 1 wherein the plurality of template means are each in the form of a flange member that is generally flat, having a generally L shaped configuration, and the flange includes a pair of spaced apart openings including a first opening that registers upon the instrument frame and a second opening that defines the respective pattern.

5. The apparatus of claim 1 wherein the indexing means comprises a plurality of shoulders spaced vertically along the instrument frame at different elevational positions, and each of the templates is sized and shaped to register upon the instrument frame at a different elevational position by registering upon a different shoulder.

6. An in-situ surgical orthopedic milling apparatus comprising:
   a) an instrument frame having upper and lower end portions;
   b) a plurality of templates having a corresponding plurality of respective patterns that constrain cutting instrument movement;
   c) a cutting device for cutting bone tissue within the intramedullary canal of a patient's bone;
   d) a stabilizer for controlling or maintaining an orthogonal relationship between the cutting tool and the top, bottom, or the periphery or the template;
   e) indexing means for affixing a selected template to the instrument frame at a selected elevational position to define an operative position;
   f) the pattern of at least some of the templates comprising a rail portion that limits travel of the cutter beyond an area defined by the pattern so that inadvertent excessive cutting is prevented; and
   g) means for supporting the instrument frame in-situ upon a patient's bone to be milled during surgery.

7. The surgical orthopedic milling apparatus of claim 6 wherein the instrument frame provides a generally vertically extending member and the templates are spaced laterally away from the vertically extending member during use.

8. The surgical orthopedic milling apparatus of claim 6 wherein the instrument frame provides at its lower end portion the means for supporting the instrument frame in-situ upon a patient's bone during use.

9. The surgical orthopedic milling apparatus of claim 6 wherein the cutter is a rotary cutting member.

10. The surgical orthopedic milling apparatus of claim 6 wherein the indexing means comprises a plurality of means for affixing the position of a particular template means at a particular elevational position along the instrument frame.

11. The surgical orthopedic milling apparatus of claim 6 wherein the instrument frame has a central vertical axis and the indexing means comprises a plurality of shoulders spaced at different elevational positions along the instrument frame, and each of the shoulders is spaced a different distance away from the instrument frame central vertical axis.

12. An in-situ surgical orthopedic milling apparatus comprising:
   a) an instrument frame having upper and lower end portions;
   b) a plurality of template means having a corresponding plurality of respective patterns;
   c) cutting means supported upon the instrument frame for cutting bone tissue within the intramedullary canal of a patient's bone;
   d) indexing means for affixing a selected template means to the instrument frame at one of a plurality of selected differing elevational positions to define an operative position;
   e) at least some of template means being removable from an operative position upon the frame when another template means is in the operative position; and
   f) means for supporting the instrument frame in-situ in a position adjacent a patient's bone to be milled.

* * * * *